(12) United States Patent  (10) Patent No.: US 8,637,677 B2
Gou et al.  (45) Date of Patent: Jan. 28, 2014

(54) ORGANIC DICARBOXYLIC ACIDS, SALTS AND PREPARATION METHOD THEREOF

(75) Inventors: Shaohua Gou, Jiangsu (CN); Hong Shen, Jiangsu (CN); Yindi Zhang, Jiangsu (CN); Jianping Shen, Jiangsu (CN); Yanqin Zhu, Jiangsu (CN); Luzhong Feng, Jiangsu (CN); Jianwei Wu, Zhejiang (CN); Dekang Chen, Zhejiang (CN)

(73) Assignees: Southeast University (CN); Nanjing Medical University (CN); Zhejiang Shapuaisi Pharmacy Ltd. (CN)

( * ) Notice: Subject to any disclaimer, the term of this patent is extended or adjusted under 35 U.S.C. 154(b) by 0 days.

(21) Appl. No.: 13/509,985

(22) PCT Filed: Nov. 12, 2010

(86) PCT No.: PCT/CN2010/078691
§ 371 (c)(1),
(2), (4) Date: May 15, 2012

(87) PCT Pub. No.: WO2011/057580
PCT Pub. Date: May 19, 2011

(65) Prior Publication Data
US 2012/0226051 A1  Sep. 6, 2012

(30) Foreign Application Priority Data
Nov. 16, 2009 (CN) .......................... 2009 1 0212692

(51) Int. Cl.
*C07D 231/56* (2006.01)
(52) U.S. Cl.
USPC ..................................... 548/339.1; 548/361.5

(58) Field of Classification Search
None
See application file for complete search history.

(56) References Cited

FOREIGN PATENT DOCUMENTS

| CN | 101703503 | 12/2010 | .......... A61K 31/416 |
| CN | 101704785 | 12/2010 | .......... C07D 231/56 |

OTHER PUBLICATIONS

International Search Report issued in Corresponding Application No. PCT/CN2010/078691 dated Feb. 24, 2011 (3 pgs).
Yanyan et al., "Synthesis of Bendazac Lysine," Chemical Industry Times, Apr. 4, 2006, vol. 20, No. 4, pp. 38-39 (2 pgs).

*Primary Examiner* — Kamal Saeed
(74) *Attorney, Agent, or Firm* — Hayes Soloway P.C.

(57) ABSTRACT

Organic dicarboxylic acid compounds, salts and preparation methods thereof are described. The compounds have activity of resisting oxidation damage to crystalline lens of eyes. The structures of the above organic dicarboxylic acid compounds are shown as

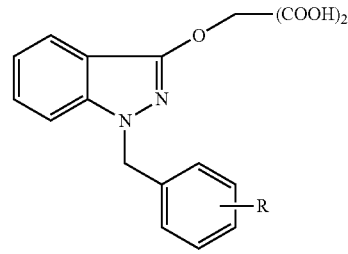

wherein R is a hydrogen atom, a $C_{1-3}$ alkyl group, a $C_{1-3}$ alkoxyl group, or a halogen atom.

7 Claims, No Drawings

ORGANIC DICARBOXYLIC ACIDS, SALTS AND PREPARATION METHOD THEREOF

FIELD OF THE INVENTION

The present invention relates to organic dicarboxylic acids, salts and the preparation method thereof, as well as the activity of resisting oxidative damage to crystalline lens of some typical compounds in the said salts.

BACKGROUND OF THE INVENTION

Cataract is one of the most common eye diseases which lead to blindness. The blindness caused by cataract accounts for about 40% of the blind people all over the world. With the coming of the aging society, the incidence of senile cataract gradually increases, thus cataract has become a worldwide common and frequently occurring disease. Though crystalline lens deprived of vision can be removed and replaced with artificial crystalline lens by operations, the cost for such operations is high and certain risks may be encountered. Therefore, more patients require drug therapy to postpone the progression of crystalline lens opacification at the initial stage in order to avoid the loss of vision, postpone or avoid operations. It has been known that bendazac lysine has certain effects in resisting cataract and it also has certain therapeutic efficacy on polysaccharide cataract when used as aldose reductase inhibitor, but this drug has irritation on eyes and its therapeutic efficacy is still insufficient. Therefore, it is essential to develop a new generation of drugs to treat cataract.

CONTENTS OF THE INVENTION

Purpose of the Invention

The present invention provides organic dicarboxylic acids, salts and preparation method thereof, wherein said compounds can be used as drugs for treating cataract.

Technical Solution

The present invention designs and synthesizes 2-(1-benzyl (or substituent benzyl)-1H-indazole-3-oxyl) malonic acid, which is used as organic diacid to react with base metal ions, ammonium ion or amino acids to prepare a series of organic malonates with novel structures. The purpose is to meet the required low-toxicity, low-irritation, excellent water solubility and effective activity of antioxidation of crystalline lens in order to treat human cataract. The present invention discloses a group of dicarboxylic acids and its salts with novel structures. Using 2-(1-benzyl (or substituent benzyl)-1H-indazole-3-oxyl) malonic acid as the organic dicarboxylic acid, the structure of these compounds can be shown by formula (1),

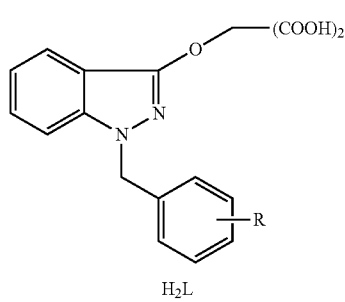

Formula (1)

$H_2L$ wherein, R is hydrogen atom, $C_{1-3}$ alkyl group, $C_{1-3}$ alkoxyl or halogen atom, and the compound shown in formula (1) is abbreviated as $H_2L$.

When the organic dioic acid shown in formula (1) reacts with the cation M to form salt, the salt can be represented by formula (2),

$M_2L$           formula (2)

wherein, M stands for monovalent cation, such as $Na^+$, $K^+$, $NH_4^+$, etc.

When the organic dioic acid shown in formula (1) reacts with amino acids to form salt, the salt can be represented by formula (3),

$A_2H_2L$           formula (3)

wherein, A stands for amino acids, such as lysine (including L-lysine, D-lysine, and the raceme composed of L-lysine and D-lysine), histidine (including L-histidine, D-histidine, and the raceme composed of L-histidine and D-histidine), etc.

Another purpose of the present invention is to provide the method for preparing the organic dicarboxylic acid shown in formula (1), which can be obtained from the reaction shown in formula (4),

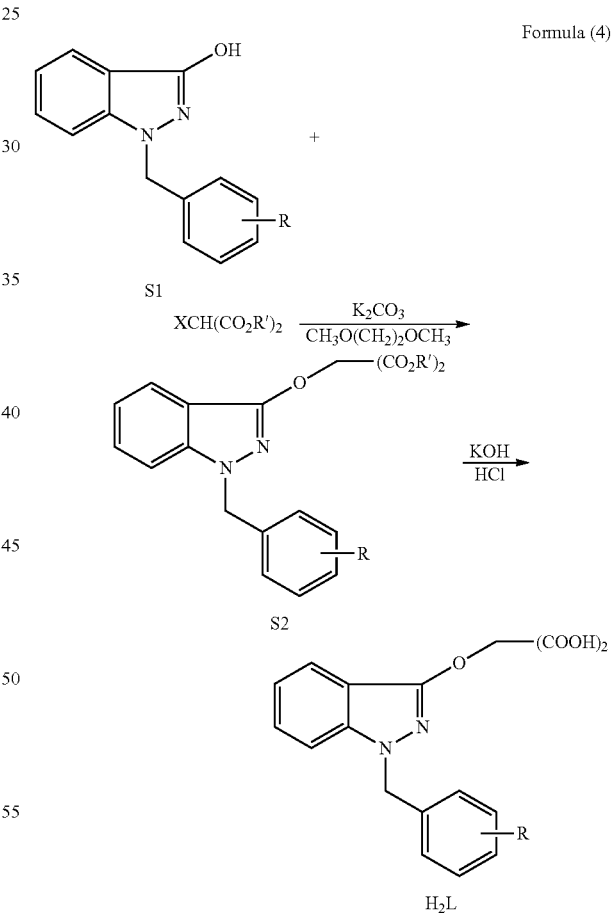

Formula (4)

wherein, X stands for Cl, Br or I atom, the definition for R is the same as that in formula (1), and R' stands for $C_{1-4}$ alkyl group. In the synthesis for these organic diacids, 1-benzyl (or substituent benzyl)-1H-indazole-3-alcohol (abbreviated as S1) reacts with α-halogenated malonic diester at the presence of alkali to obtain 2-(1-benzyl (or substituent benzyl)-1H-indazole-3-oxyl) malonic diester (abbreviated as S2). Afterwards, the ester is hydrolyzed under alkaline conditions, and then after acidification the corresponding organic diacid ($H_2L$) is obtained.

The detailed synthetic process is as followed: 1.0 mole of S1 is subjected to reflux reaction with 1.2 mole of XCH$(CO_2R')_2$ at the presence of 2.5 moles of potassium carbonate in the solvent of glycol dimethyl ether to obtain S2, subsequently S2 is subjected to reflux hydrolysis in potassium hydroxide (or sodium hydroxide) solution, and then acidified to pH of about 2 with diluted hydrochloric acid, finally $H_2L$ is obtained.

The organic diacid ($H_2L$) shown in formula (1) is subjected to reaction with corresponding alkali, such as sodium hydroxide, potassium hydroxide, aqueous ammonia, etc., to obtain the salt ($M_2L$) shown in formula (2); the organic diacid ($H_2L$) shown in formula (1) is subjected to reaction with corresponding amino acid, such as lysine (including L-lysine, D-lysine, and the raceme composed of L-lysine and D-lysine), histidine (including L-histidine, D-histidine, and the raceme composed of L-histidine and D-histidine) or other amino acids, to produce the salt ($A_2H_2L$) as shown in formula (3).

The structures of the prepared compounds in the present invention have been confirmed by different analytical methods such as infrared spectra, proton nuclear magnetic resonance spectra, organic mass spectrometry or electrospray ionization mass spectrometry.

Beneficial Effects

The present invention provides a kind of organic dicarboxylic acid, salt and preparation method thereof, and it discloses the activity of resisting oxidative damage to crystalline lens of some typical organic dicarboxylate compounds, the irritation to the eyes of which is lower than those of existing drugs, and the therapeutic efficacy of which is better.

Embodiments

The present invention is further illustrated by the following embodiments, but this invention is not restricted to these embodiments.

Example 1

Preparation of 2-(1-benzyl(or substituent benzyl)-1H-indazole-3-oxyl) malonic ester 12 g (0.090 mol) 3-hydroxyl-indazole (J & K Scientific), 3.94 g (0.098 mol) sodium hydroxide and 90 mL water is added into a 250 mL three-necked bottle and agitated at 40° C. for 10 min, then 0.090 mol benzyl chloride (or substituent benzyl chloride) is dropwise added in and the mixture is reacted at 70° C. for 2 h with solids being precipitated out, filter, the filter cake is washed with water and finally 1-benzyl (or substituent benzyl)-1H-indazole-3-alcohol is obtained.

40 mL glycol dimethyl ether (solvent) is added into a 100 mL four-necked bottle, then 1-benzyl(or substituent benzyl)-1H-indazole-3-alcohol (10.5 mmol) and 3.6 g (26.1 mmol) potassium carbonate are mixed in the four-necked bottle. The mixture is agitated at room temperature for 10 min, subsequently 3.0 g (12.6 mmol) brominated diethyl malonate (J & K Scientific) is dropwise added, afterwards the mixture is heated and subjected to reflux for 4 h, filter after the solution changes from yellow into reddish brown. The filtrate is concentrated and subjected to column chromatography (developing agent: petroleum ether (60-90° C.): ethyl acetate=1:1), and following products can be obtained:

(1) 2-(1-benzyl-1H-indazole-3-oxyl)diethyl malonate (S2-1)
Yield: 39%
IR(KBr, $cm^{-1}$): 2981 (m), 1768 (s), 1748 (s), 1619 (m), 1235 (s), 744 (m)
EI-MS: 382 [$M^+$]
$^1$HNMR (500 MHz, $CDCl_3$), δ(ppm): 1.29~1.33 (t, 6H, $CH_2CH_3$), 4.29~4.33 (dd, 4H, $CH_2CH_3$), 5.34 (s, 2H, $CH_2C_6H_5$), 5.77 (s, 1H, CH(COOH)$_2$), 7.08~7.83 (m, 9H, 2Ar)

(2) 2-[1-(4-methyl-benzyl)-1H-indazole-3-oxyl]diethyl malonate (S2-2)
Yield: 29%
IR(KBr, $cm^{-1}$): 2985(w), 1764(s), 1743(s), 1617(m), 1225(s), 749(m)
EI-MS: 396 [$M^+$]
$^1$HNMR (500 MHz, $CDCl_3$), δ(ppm): 1.28~1.31 (t, 6H, $CH_2CH_3$), 2.40 (s, 3H, $CH_2C_6H_4CH_3$), 4.29~4.33 (dd, 4H, $CH_2CH_3$), 5.36 (s, 2H, $CH_2C_6H_4CH_3$), 5.79 (s, 1H, CH(COOH)$_2$), 7.02~7.80 (m, 8H, 2Ar)

(3) 2-[1-(3-fluorine-benzyl)-1H-indazole-3-oxyl]diethyl malonate (S2-3)
Yield: 56%
IR(KBr, $cm^{-1}$): 2983(w), 1767(s), 1748(s), 1618(m), 1253(s), 745(m)
EI-MS: 400 [$M^+$]
$^1$HNMR (500 MHz, $CDCl_3$), δ(ppm): 1.28~1.33 (t, 6H, $CH_2CH_3$), 4.27~4.34 (dd, 4H, $CH_2CH_3$), 5.33 (s, 2H, $CH_2C_6H_4F$), 5.76 (s, 1H, CH(COOH)$_2$), 6.80~7.83 (m, 8H, 2Ar)

(4) 2-[1-(3-chloro-benzyl)-1H-indazole-3-oxyl]diethyl malonate (S2-4)
Yield: 51%
IR(KBr, $cm^{-1}$): 2984(m), 1735(s), 1619(w), 1247(s), 747 (m)
ESI-MS: 439 [$M+Na$]$^+$
$^1$HNMR (500 MHz, $CDCl_3$), δ(ppm): 1.28~1.33 (t, 6H, $CH_2CH_3$), 4.31~4.35 (dd, 4H, $CH_2CH_3$), 5.29 (s, 2H, $CH_2C_6H_4Cl$), 5.76 (s, 1H, CH(COOH)$_2$), 7.02~7.83 (m, 8H, 2Ar)

(5) 2-[1-(4-chloro-benzyl)-1H-indazole-3-oxyl]diethyl malonate (S2-5)
Yield: 18%
IR(KBr, $cm^{-1}$): 2982(w), 1764(s), 1740(s), 1616(w), 1222 (s), 746(m)
ESI-MS: 439 [$M+Na$]$^+$
$^1$HNMR (500 MHz, $CDCl_3$), δ(ppm): 1.27~1.34 (t, 6H, $CH_2CH_3$), 4.28~4.32 (dd, 4H, $CH_2CH_3$), 5.29 (s, 2H, $CH_2C_6H_4Cl$), 5.74 (s, 1H, CH(COOH)$_2$), 7.04~7.81 (m, 8H, 2Ar)

Example 2

Preparation of 2-(1-Benzyl (or Substituent Benzyl)-1H-Indazole-3-Oxyl) Malonic Acids The esters (2.7 mmol) obtained from the example 1 are added into 10 ml aqueous solution of 0.3 g potassium hydroxide (5.4 mmol) respectively, and the mixture is heated and subjected to reflux for 2 h, subsequently the pH of the mixture is adjusted to 2 by 1M hydrochloric acid, white solids are precipitated, filtered and washed with small amount of water, and the following compounds can be obtained after drying:

(1) 2-(1-benzyl-1H-indazole-3-oxyl) malonic acid ($H_2L^1$)
Yield: 93%

Mp: 182-186° C. (decomposition)

IR(KBr, cm$^{-1}$): 3033(m), 2934(m), 1741(s), 1620(m), 1257(s), 746(m), 711(m)

ESI-MS: 325 [M−H]$^-$ $^1$HNMR (500 MHz, D$_2$O), δ(ppm): 5.30 (s, 2H, CH$_2$C$_6$H$_5$), 5.36 (s, 1H, CH(COOH)$_2$), 7.00~7.73 (m, 9H, 2Ar);

(2) 2-[1-(4-methyl-benzyl)-1H-indazole-3-oxyl)malonic acid (H$_2$L$^2$)

Yield: 98%

Mp: 144-146° C.

IR(KBr, cm$^{-1}$): 3023(m), 2920(m), 1755(s), 1618(m), 1255(s), 744(s), 727(m)

ESI-MS: 379 [M+K]$^+$ $^1$HNMR (500 MHz, D$_2$O), δ(ppm): 2.16 (s, 3H, CH$_2$C$_6$H$_4$CH$_3$), 5.29 (s, 2H, CH$_2$C$_6$H$_4$CH$_3$), 5.46 (s, 1H, CH(COOH)$_2$), 6.97-7.75 (m, 8H, 2Ar);

(3) 2-[1-(3-fluorine-benzyl)-1H-indazole-3-oxyl]malonic acid (H$_2$L$^3$)

Yield: 96%

Mp: 138-140° C.

IR(KBr, cm$^{-1}$): 3065(m), 2925(w), 1732(s), 1618(m), 1254(s), 743 (s)

ESI-MS: 383 [M+K]$^+$, 367 [M+Na]$^+$, 345 [M+H]$^+$ $^1$HNMR (500 MHz, D$_2$O), δ(ppm): 5.41 (s, 2H, CH$_2$C$_6$H$_4$F), 5.49 (s, 1H, CH(COOH)$_2$), 6.82~7.85 (m, 8H, 2Ar);

(4) 2-[1-(3-chloro-benzyl)-1H-indazole-3-oxyl]malonic acid (H$_2$L$^4$)

Yield: 98%

Mp: 137-139° C.

IR(KBr, cm$^{-1}$): 3063(m), 2940(m), 1749(s), 1619(m), 1247(s), 745(s), 725(m)

ESI-MS: 399 [M+K]$^+$, 361 [M+H]$^+$ $^1$HNMR (500 MHz, D$_2$O), δ(ppm): 5.40 (s, 2H, CH$_2$C$_6$H$_4$Cl), 5.51 (s, 1H, CH(COOH)$_2$), 7.04~7.85 (m, 8H, 2Ar);

(5) 2-[1-(4-chloro-benzyl)-1H-indazole-3-oxyl]malonic acid (H$_2$L$^5$)

Yield: 88%

Mp: 114-116° C.

ESI-MS: 399 [M+K]$^+$, 361[M+H]$^+$

IR(KBr, cm$^{-1}$): 3064(m), 2921(m), 1747(s), 1619(m), 1251(s), 740(s)

$^1$HNMR (500 MHz, D$_2$O), δ(ppm): 5.32 (s, 2H, CH$_2$C$_6$H$_4$Cl), 5.46 (s, 1H, CH(COOH)$_2$), 7.01~7.78 (m, 8H, 2Ar)

Example 3

Preparation of 2-(1-benzyl (or substituent benzyl)-1H-indazole-3-oxyl) malonates 2.0 mmol acids obtained from the example 2 are added into 5 mL water respectively and agitated for 5 min, 5 mL aqueous solution of 4.0 mmol alkali or 4.0 mmol amino acids is dropwise added, subsequently the mixture is agitated at room temperature for 4 h and concentrated under reduced pressure to remove water, and then oil-like substance is obtained, afterwards 20 mL dehydrated alcohol is added, the mixture is filtered after solids are precipitated, the filter cake is washed with 2 mL dehydrated alcohol and then subjected to vacuum drying, finally the following products can be obtained:

(1) 2-(1-benzyl-1H-indazole-3-oxyl) malonate disodium (Y1)

Yield: 75%

IR(KBr, cm$^{-1}$): 2983(w), 1643(s), 1334(m), 741(m), 723 (m)

$^1$HNMR (500 MHz, D$_2$O), δ(ppm): 5.21 (s, 1H, CH(COO$^-$)$_2$), 5.33 (s, 2H, CH$_2$C$_6$H$_5$), 7.03~7.79 (m, 9H, 2Ar)

(2) 2-(1-benzyl-1H-indazole-3-oxyl) malonate dipotassium (Y2)

Yield: 86%

IR(KBr, cm$^{-1}$): 2978(w), 1639(s), 1328(m), 740(m), 721 (m)

$^1$HNMR (500 MHz, D$_2$O), δ(ppm): 5.23 (s, 1H, CH(COO$^-$)$_2$), 5.35 (s, 2H, CH$_2$C$_6$H$_5$), 6.97~7.78 (m, 9H, 2Ar)

(3) 2-(1-benzyl-1H-indazole-3-oxyl) malonate diammonium (Y3)

Yield: 75%

IR(KBr, cm$^{-1}$): 3197(s), 1593(s), 1326(s), 1105(m), 771(s), 746(m)

$^1$HNMR (500 MHz, D$_2$O), δ(ppm): 5.22 (s, 1H, CH(COO$^-$)$_2$), 5.34 (s, 2H, CH$_2$C$_6$H$_5$), 7.03~7.81 (m, 9H, 2Ar)

(4) 2-(1-benzyl-1H-indazole-3-oxyl) malonate dihistidine (Y4)

Yield: 92%

IR(KBr, cm$^{-1}$): 3128(m), 3026(m), 1618(s), 1329(m), 1259(w), 744(m)

$^1$HNMR (500 MHz, D$_2$O), δ(ppm): 3.10~3.24 (m, 4H, 2CH$_2$ of Histidine), 3.89~3.94 (m, 2H, 2CHNH$_2$COOH of Histidine), 5.28 (s, 1H, CH(COO$^-$)$_2$), 5.34 (s, 2H, CH$_2$C$_6$H$_5$), 7.05~7.80 (m, 11H, 9H of 2Ar, and 2H of 2 Imidazole), 8.27 (s, 2H, 2H of 2 Imidazole)

(5) 2-(1-benzyl-1H-indazole-3-oxyl) malonate dilysine (Y5)

Yield: 86%

IR(KBr, cm$^{-1}$): 3031(s), 2941(s), 1615(s), 1325(m), 741 (m)

$^1$HNMR (500 MHz, D$_2$O), δ(ppm): 1.30~1.43 (m, 4H, 2H$_2$NC$_2$H$_4$CH$_2$CH$_2$ of Lysine), 1.60~1.63 (m, 4H, 2H$_2$NC$_2$H$_4$CH$_2$CH$_2$ of Lysine), 1.78~1.82 (m, 4H, 2H$_2$NCH$_2$CH$_2$C$_2$H$_4$ of Lysine), 2.90~2.93 (m, 4H, 2H$_2$NCH$_2$CH$_2$C$_2$H$_4$ of Lysine), 3.65 (m, 2H, 2CH(NH$_2$)COOH of Lysine), 5.24 (s, 1H, CH(COO$^-$)$_2$), 5.36 (s, 2H, CH$_2$C$_6$H$_5$), 7.09~7.81 (m, 9H, 2Ar)

(6) 2-[1-(4-methyl-benzyl)-1H-indazole-3-oxyl) malonate disodium (Y6)

Yield: 76%

IR(KBr, cm$^{-1}$): 2983(m), 1621(s), 1336(s), 1256(m), 746 (m)

$^1$HNMR (500 MHz, D$_2$O), δ(ppm): 2.15 (s, 3H, C$_6$H$_4$CH$_3$), 5.22 (s, 1H, CH(COO$^-$)$_2$), 5.27 (s, 2H, CH$_2$C$_6$H$_4$CH$_3$), 6.97~7.80 (m, 8H, 2Ar)

(7) 2-[1-(4-methyl-benzyl)-1H-indazole-3-oxyl) malonate dipotassium (Y7)

Yield: 80%

IR(KBr, cm$^{-1}$): 2986(m), 1625(s), 1338(m), 1255(m), 744 (m)

$^1$HNMR (500 MHz, D$_2$O), δ(ppm): 2.17 (s, 3H, C$_6$H$_4$CH$_3$), 5.25 (s, 1H, CH(COO$^-$)$_2$), 5.30 (s, 2H, CH$_2$C$_6$H$_4$CH$_3$), 6.99~7.85 (m, 8H, 2Ar)

(8) 2-[1-(4-methyl-benzyl)-1H-indazole-3-oxyl) malonate diammonium (Y8)

Yield: 70%

IR(KBr, cm$^{-1}$): 3330(s), 2983(m), 1600(s), 1331(m), 746 (m)

$^1$HNMR (500 MHz, D$_2$O), δ(ppm): 2.13 (s, 3H, C$_6$H$_4$CH$_3$), 5.21 (s, 1H, CH(COO$^-$)$_2$), 5.28 (s, 2H, CH$_2$C$_6$H$_4$CH$_3$), 6.89~7.80 (m, 8H, 2Ar)

(9) 2-[1-(4-methyl-benzyl)-1H-indazole-3-oxyl) malonate dilysine (Y9)
Yield: 88%
IR(KBr, cm$^{-1}$): 3432(s), 2930(s), 1619(s), 1335(m), 743(m)
$^1$HNMR (500 MHz, D$_2$O), δ(ppm): 1.3~1.38 (m, 4H, 2H$_2$NC$_2$H$_4$CH$_2$CH$_2$ of Lysine), 1.54~1.64 (m, 4H, 2H$_2$NC$_2$H$_4$CH$_2$CH$_2$ of Lysine), 1.74~1.81 (m, 4H, 2H$_2$NCH$_2$CH$_2$C$_2$H$_4$ of Lysine), 2.12 (s, 3H, CH$_2$C$_6$H$_4$CH$_3$), 2.86~2.91 (m, 4H, 2H$_2$NCH$_2$CH$_2$C$_2$H$_4$ of Lysine), 3.61~3.65 (m, 2H, 2CH(NH$_2$)COOH of Lysine), 5.20 (s, 2H, CH$_2$C$_6$H$_5$CH$_3$), 5.28 (s, 1H, CH(COO$^-$)$_2$), 6.92~7.76 (m, 8H, 2Ar)

(10) 2-[1-(3-fluoro-benzyl)-1H-indazole-3-oxyl) malonate disodium (Y10)
Yield: 83%
IR(KBr, cm$^{-1}$): 2927(w), 1619(s), 1337(m), 739(m)
$^1$HNMR (500 MHz, D$_2$O), δ(ppm): 5.22 (s, 1H, CH(COOH)$_2$), 5.34 (s, 2H, CH$_2$C$_6$H$_4$F), 6.77~7.80 (m, 8H, 2Ar)

(11) 2-[1-(3-fluoro-benzyl)-1H-indazole-3-oxyl) malonate dipotassium (Y11)
Yield: 80%
IR(KBr, cm$^{-1}$): 2929(w), 1605(s), 1331(m), 741(m)
$^1$HNMR (500 MHz, D$_2$O), δ(ppm): 5.22 (s, 1H, CH(COOH)$_2$), 5.30 (s, 2H, CH$_2$C$_6$H$_4$F), 6.75~7.80 (m, 8H, 2Ar)

(12) 2-[1-(3-fluoro-benzyl)-1H-indazole-3-oxyl) malonate diammonium (Y12)
Yield: 75%
IR(KBr, cm$^{-1}$): 3340(s), 2931(w), 1641(s), 1336(m), 743(m)
$^1$HNMR (500 MHz, D$_2$O), δ(ppm): 5.35 (s, 1H, CH(COOH)$_2$), 5.43 (s, 2H, CH$_2$C$_6$H$_4$F), 6.77~7.78 (m, 8H, 2Ar)

(13) 2-[1-(3-fluoro-benzyl)-1H-indazole-3-oxyl) malonate dihistidine (Y13)
Yield: 84%
IR(KBr, cm$^{-1}$): 3154(s), 3012(m), 1600(s), 1331(m), 1226(w), 741(m)
$^1$HNMR (500 MHz, D$_2$O), δ(ppm): 3.10~3.13 (d, 4H, 2CH$_2$ of Histidine), 3.83~3.87 (m, 2H, 2CHNH$_2$COOH of Histidine), 5.22 (s, 1H, CH(COO$^-$)$_2$), 5.26 (s, 2H, CH$_2$C$_6$H$_4$F), 6.71~7.73 (m, 10H, 2Ar and 2H of 2 Imidazole of Histidine), 8.33 (s, 2H, 2 Imidazole of Histidine)

(14) 2-[1-(3-fluoro-benzyl)-1H-indazole-3-oxyl) malonate dilysine (Y14)
Yield: 85%
IR(KBr, cm$^{-1}$): 3435(s), 2931(s), 1622(s), 1328(m), 744(m)
$^1$HNMR (500 MHz, D$_2$O), δ(ppm): 1.32~1.46 (m, 4H, 2H$_2$NC$_2$H$_4$CH$_2$CH$_2$ of Lysine), 1.55~1.66 (m, 4H, 2H$_2$NC$_2$H$_4$CH$_2$CH$_2$ of Lysine), 1.72~1.79 (m, 4H, 2H$_2$NCH$_2$CH$_2$C$_2$H$_4$ of Lysine), 2.89~2.93 (m, 4H, 2H$_2$NCH$_2$CH$_2$C$_2$H$_4$ of Lysine), 3.55~3.59 (m, 2H, 2CH(NH$_2$)COOH of Lysine), 5.25 (s, 1H, CH(COO$^-$)$_2$), 5.35 (s, 2H, CH$_2$C$_6$H$_4$F), 6.80~7.87 (m, 8H, 2Ar)

(15) 2-[1-(3-chloro-benzyl)-1H-indazole-3-oxyl]malonate disodium (Y15)
Yield: 80%
IR(KBr, cm$^{-1}$): 2937(w), 1619(s), 1336(s), 744(m)
$^1$HNMR (500 MHz, D$_2$O), δ(ppm): 5.22 (s, 1H, CH(COOH)$_2$), 5.26 (s, 2H, CH$_2$C$_6$H$_4$Cl), 6.94~7.80 (m, 8H, 2Ar)

(16) 2-[1-(3-chloro-benzyl)-1H-indazole-3-oxyl]malonate dipotassium (Y16)
Yield: 78%
IR(KBr, cm$^{-1}$): 2940(w), 1605(s), 1337(s), 746(m)
$^1$HNMR (500 MHz, D$_2$O), δ(ppm): 5.39 (s, 1H, CH(COOH)$_2$), 5.43 (s, 2H, CH$_2$C$_6$H$_4$Cl), 7.08~7.95 (m, 8H, 2Ar)

(17) 2-[1-(3-chloro-benzyl)-1H-indazole-3-oxyl]malonate diammonium (Y17)
Yield: 71%
IR(KBr, cm$^{-1}$): 3250(s), 2942(m), 1641(s), 1322(m), 746(m)
$^1$HNMR (500 MHz, D$_2$O), δ(ppm): 5.23 (s, 1H, CH(COOH)$_2$), 5.33 (s, 2H, CH$_2$C$_6$H$_4$Cl), 6.76~7.81 (m, 8H, 2Ar)

(18) 2-[1-(3-chloro-benzyl)-1H-indazole-3-oxyl]malonate dihistidine (Y18)
Yield: 82%
IR(KBr, cm$^{-1}$): 3132(s), 2932(m), 1640(s), 1326(m), 742(m)
$^1$HNMR (300 MHz, D$_2$O), δ(ppm): 3.10 (m, 4H, 2CH$_2$ of Histidine), 3.81~3.83 (m, 2H, 2CHNH$_2$COOH of Histidine), 5.16 (s, 1H, CH(COO$^-$)$_2$), 5.22 (s, 2H, CH$_2$C$_6$H$_4$Cl), 6.86~7.69 (m, 10H, 8H of 2Ar and 2H of 2 Imidazole of Histidine), 8.32 (s, 2H, 2 Imidazole of Histidine)

(19) 2-[1-(3-chloro-benzyl)-1H-indazole-3-oxyl]malonate dilysine (Y19)
Yield: 91%
IR(KBr, cm$^{-1}$): 2934(m$_2$), 1613(s), 1320(m), 1105(m), 741(m$_4$)
$^1$HNMR (500 MHz, D$_2$O), δ(ppm): 1.26~1.34 (m, 4H, 2H$_2$NC$_2$H$_4$CH$_2$CH$_2$ of Lysine), 1.49~1.56 (m, 4H, 2H$_2$NC$_2$H$_4$CH$_2$CH$_2$ of Lysine), 1.72~1.74 (m, 4H, 2H$_2$NCH$_2$CH$_2$C$_2$H$_4$ of Lysine), 2.81~2.86 (m, 4H, 2H$_2$NCH$_2$CH$_2$C$_2$H$_4$ of Lysine), 3.52~3.62 (m, 2H, 2CH(NH$_2$)COOH of Lysine), 5.13 (s, 2H, CH$_2$C$_6$H$_4$Cl), 5.21 (s, 1H, CH(COO$^-$)$_2$), 6.88~7.76 (m, 8H, 2Ar)

(20) 2-[1-(4-chloro-benzyl)-1H-indazole-3-oxyl]malonate disodium (Y20) Yield: 84%
IR(KBr, cm$^{-1}$): 2980(w), 1642(s), 1336(m), 739(m)
$^1$HNMR (500 MHz, D$_2$O), δ(ppm): 5.16 (s, 2H, CH$_2$C$_6$H$_4$Cl), 5.22 (s, 1H, CH(COOH)$_2$), 6.92~7.76 (m, 8H, 2Ar)

(21) 2-[1-(4-chloro-benzyl)-1H-indazole-3-oxyl]malonate dipotassium (Y21)
Yield: 82%
IR(KBr, cm$^{-1}$): 2982(w), 1636(s), 1325(m), 741(m)
$^1$HNMR (500 MHz, D$_2$O), δ(ppm): 5.18 (s, 1H, CH(COOH)$_2$), 5.24 (s, 2H, CH$_2$C$_6$H$_4$Cl), 6.99~7.83 (m, 8H, 2Ar)

(22) 2-[1-(4-chloro-benzyl)-1H-indazole-3-oxyl]malonate diammonium (Y22)
Yield: 78%
IR(KBr,cm$^{-1}$): 3232(s), 2985(w), 1612(s), 1323(m), 743(m)
$^1$HNMR (500 MHz, D$_2$O), δ(ppm): 5.24 (s, 1H, CH(COOH)$_2$), 5.31 (s, 2H, CH$_2$C$_6$H$_4$Cl), 7.08~7.96 (m, 8H, 2Ar)

(23) 2-[1-(4-chloro-benzyl)-1H-indazole-3-oxyl]malonate dihistidine (Y23)
Yield: 94%
IR(KBr, cm$^{-1}$): 3162(m), 2978(m), 1638(s), 1315(m), 746(m)
$^1$HNMR (500 MHz, D$_2$O), δ(ppm): 3.00~3.14 (m, 4H, 2CH$_2$ of Histidine), 3.81~3.85 (m, 2H, 2CHNH$_2$COOH of Histidine), 5.19 (s, 1H, CH(COO$^-$)$_2$), 5.25 (s, 2H, CH$_2$C$_6$H$_4$Cl), 6.93~7.71 (m, 10H, 8H of 2Ar and 2H of 2 Imidazole of Histidine), 812 (s, 2H, 2 Imidazole of Histidine)

(24) 2-[1-(4-chloro-benzyl)-1H-indazole-3-oxyl]malonate dilysine (Y24)

Yield: 93%

IR(KBr, cm$^{-1}$): 2930(m), 1619(s), 1316(m), 1108(m), 740(s)

$^1$HNMR (500 MHz, D$_2$O), δ(ppm): 1.24~1.32 (m, 4H, 2H$_2$NC$_2$H$_4$CH$_2$CH$_2$ of Lysine), 1.48~1.58 (m, 4H, 2H$_2$NC$_2$H$_4$CH$_2$CH$_2$ of Lysine), 1.65~1.67 (m, 4H, 2H$_2$NCH$_2$CH$_2$C$_2$H$_4$ of Lysine), 2.80~2.85 (m, 4H, 2H$_2$NCH$_2$CH$_2$C$_2$H$_4$ of Lysine), 3.45~3.53 (m, 2H, 2CH(NH$_2$)COOH of Lysine), 5.19 (s, 1H, CH(COO$^-$)$_2$), 5.21 (s, 2H, CH$_2$C$_6$H$_4$Cl), 6.95~7.75 (m, 8H, 2Ar)

Activities of Typical Compounds

Some typical compounds are selected for the research on the capability of in vitro resisting oxidative damage to crystalline lens induced by H$_2$O$_2$. The experiments are illustrated as follows:

1. Culture of Eye Crystalline Lens

Kill rats and rabbits, take out their eyeballs and rinse with saline containing 500 u/mL penicillin, split the eyeball from the posterior to remove eyeball wall and vitreous body, strip off the suspensory ligament, take out the crystalline lens and wash with PBS solution containing 500 u/mL penicillin and 0.5 mg/mL streptomycin for 5 min Before experiment, check with anatomical lens to confirm that there is no opacification or other abnormal condition in the crystalline lens, then place the crystalline lens in the sterilized 12-well plate containing 2 mL DMEM/high glucose (a product from Beijing Thermo Fisher Scientific Biochemical Product Co., Ltd.) sterile culture solution (which contains 100 u/mL penicillin and 0.1 mg/mL streptomycin), add different compounds for screening and pre-culture in a incubator with temperature of 37° C., humidity of 95% and 5% CO$_2$ for 1 h, subsequently add 2 mL DEME culture solution containing H$_2$O$_2$ and FeCl$_3$ (namely, total 4 mL culture solution in each well) (the total concentration of H$_2$O$_2$ in each well is 2% for rabbits, and 5% for rats, and the concentrations of FeCl$_3$ are all 0.02%), culture under the same conditions for 24 hours. The experiments are divided into several groups as below and carried out in batches, with each batch provided with negative control group and model group.

A. Negative control group: DMEM culture solution without H$_2$O$_2$.

B. Model group (oxidative damage group): DMEM culture solution containing H$_2$O$_2$ and FeCl$_3$.

C. Vitamin C group: besides the ingredients of the model group, further containing vitamin C (the final concentration is 1 mmol/L).

D. Bendazac lysine (BDL) group (BDL is provided by Zhejiang Shapuaisi Pharmaceutical Co. Ltd., and its purity is more than 98.5%): besides the ingredients of model group, further containing BDL (the final concentration is 0.5 mmol/L).

E. Sample group: besides the ingredients of model group, further containing sample (the final concentration is 0.5 mmol/L).

2. Morphological Observations

After 24 h culture, observe the opacification degree of eye crystalline lens, take photograph under the background with black "+" in different thickness on white ground below the 12-well plate, score and divide into three different grades:

– indicates normal transparent lens;

+ indicates mild opacity (the first "+" is slightly ambiguous but is still clearly visible, the second "+" is clear); degree I ++ indicates moderate opacity (the second "+" is slightly ambiguous but is still clearly visible, the third "+" is clear); degree II +++ indicates that the lens are totally opacified (the third "+" f is not clearly visible); degree III 3. Results The results for the capabilities of the sample compounds in resisting oxidative damage to in vitro eye lens of rabbits induced by H$_2$O$_2$ are shown in table 1; and the results for the capabilities of the sample compounds in resisting oxidative damage to in vitro eye lens of rats induced by H$_2$O$_2$ are shown in table 2.

According to table 1, the compounds showing inhibitory effects on oxidative damage to in vitro eye lens of rabbits induced by H$_2$O$_2$ are Y4 and Y10, and the inhibitory effects of Y1, Y2, Y5 and Y19 on oxidative damage to in vitro eye lens of rabbits induced by H$_2$O$_2$ are not significant.

According to table 2, the compounds showing inhibitory effects on oxidative damage to in vitro eye lens of rats induced by H$_2$O$_2$ are Y1, Y4, Y5, Y14 and Y19, and the inhibitory effects of Y2 and Y10 on oxidative damage to in vitro eye lens of rats induced by H$_2$O$_2$ are not significant.

TABLE 1 the capabilities of the sample compounds in resisting oxidative damage to in vitro eye lens of rabbits induced by H$_2$O$_2$

| | Observation Results | | | | | Percentages for different degrees % | | |
|---|---|---|---|---|---|---|---|---|
| | – | + | ++ | +++ | Total | – | + Degree (I) | >++ Degrees(I, II) | Comments |
| A (the negative control group) | 61 | | | | 61 | 100 | | | |
| B (the model group) | | 26 | 31 | 22 | 79 | | 33 | 67 | |
| C (the VC group) | | 13 | 16 | 2 | 31 | | 42 | 58 | |
| D (the BDL group) | | 9 | 3 | | 12 | | 75 | 25 | ✓ |
| Y1 | | 4 | 3 | | 7 | | 57 | 43 | |
| Y2 | | 2 | 3 | 2 | 7 | | 29 | 71 | |
| Y4 | | 14 | 7 | | 21 | | 67 | 33 | ✓ |
| Y5 | | 2 | 2 | 2 | 6 | | 33 | 67 | |
| Y10 | | 4 | 1 | | 5 | | 80 | 20 | ✓ |
| Y19 | | | | 3 | 3 | | | 100 | |

Evaluation criteria: according to large amount of experiments on the model group, the ratio between the percentage of different degrees of lens opacification in the groups and the percentage of different degrees of lens opacification in the model group is utilized as the definition, wherein, for slight improvement (√), the percentage of ++ (degrees II, III) should be lower than 67%, and the percentage of + (degree I) should be higher than 33%; for moderate improvement (√√), the percentage of ++(degrees II, III) further decreases; and the percentage of 0 (−) appears; for significant improvement (√√√), the percentage of ++ (degrees II, III) and + (degree I) disappears, and the lens are almost transparent.

TABLE 2 the capabilities of the sample compounds in resisting oxidative damage to in vitro eye lens of rats induced by $H_2O_2$

| | Observation Results | | | | | Percentages % | | | |
|---|---|---|---|---|---|---|---|---|---|
| | − | + | ++ | +++ | Total | − | + Degree (I) | >++ Degrees (II, III) | Comments |
| A (the negative control group) | 84 | 9 | 12 | 13 | 118 | 71 | 8 | 21 | |
| B (the model group) | 15 | 18 | 47 | 36 | 116 | 13 | 15 | 72 | |
| C (the VC group) | | 7 | 8 | 3 | 18 | | 39 | 61 | |
| D (the BDL group) | | 30 | 22 | 3 | 55 | | 54 | 46 | ✓ |
| Y1 | | 4 | 1 | | 5 | | 80 | 20 | ✓ |
| Y2 | | | 3 | 3 | 6 | | | 100 | |
| Y4 | | 18 | 3 | | 21 | | 86 | 14 | ✓ |
| Y5 | | 1 | 4 | 1 | 6 | | 17 | 83 | |
| Y10 | | 47 | 28 | 3 | 78 | | 60 | 40 | ✓ |
| Y14 | | 10 | 8 | | 18 | | 56 | 44 | ✓ |
| Y19 | | 18 | 10 | 4 | 32 | | 56 | 44 | ✓ |

Evaluation criteria: according to large amount of experiments on the model group, the ratio between the percentage of different degrees of lens turbidity in the groups and the percentage of different degrees of lens turbidity in the model group is utilized as the definition, wherein, for slight improvement (√), the percentage of ++ (degrees II, III) should be lower than 72%, and the percentage of + (degree I) should be higher than 20%; for moderate improvement (√√) the percentage of ++(degrees II, III) further decreases; and the percentage of 0 (−) appears; for significant improvement (√√√), the percentage of ++ (degrees II, III) and +(degree I) disappears, and the lens are almost transparent.

The invention claimed is:

1. An organic compound of the formula (I):

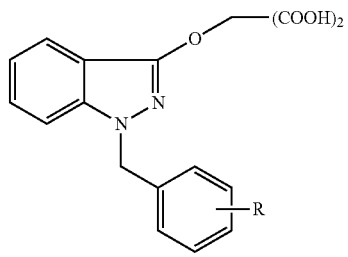

(I)

wherein, R is selected from the group consisting of a hydrogen atom, a $C_{1-3}$ alkyl group, a $C_{1-3}$ alkoxyl group, and a halogen atom.

2. A dicarboxylate of the compound of claim 1, wherein the dicarboxylate is formed through a reaction of a dicarboxylic acid group in the compound of formula (I) and monovalent cation selected from the group consisting of $Na^+$, $K^+$ and $NH_4^+$.

3. A dicarboxyate of the compound of claim 1, wherein the dicarboxylate is formed through a reaction of a dicarboxylic acid group in the compound of formula (I) and an amino acid selected from the group consisting of a lysine and a histidine.

4. The dicarboxylate of claim 3, wherein the lysine is selected from the group consisting of L-lysine, D-lysine, and a raceme comprising L-lysine and D-lysine.

5. The dicarboxylate of claim 3, wherein the histidine is selected from the group consisting of L-histidine, D-histidine, and a raceme comprising L-histidine and D-histidine.

6. A method for preparing the compound of claim 1, which comprises reacting a compound of the formula (II):

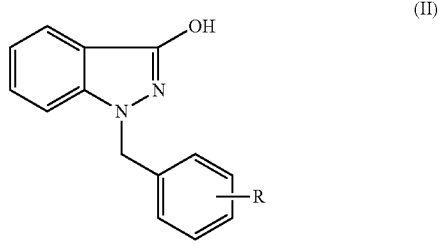

(II)

with a compound of the formula $XCH(CO_2R')_2$, under alkaline conditions to obtain a compound of formula (III):

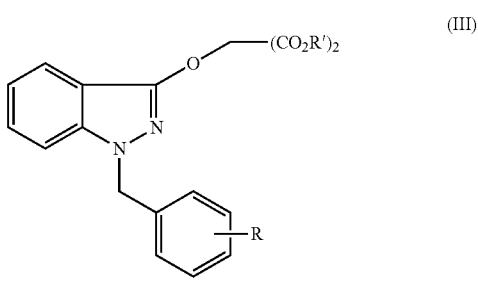

(III)

hydrolyzing the compound of the formula III under alkaline conditions, and then acidifying the resulting compound to obtain a compound of the formula (I):

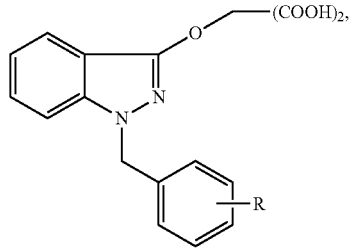
(I)

wherein, X is selected from the group consisting of Cl, Br or I, R is selected from the group consisting of a hydrogen atom, a $C_{1-3}$ alkyl group, a $C_{1-3}$ alkoxyl group and halogen atom, and R' is a $C_{1-4}$ alkyl group.

7. The method according to claim 6, wherein 1.0 mole of the compound of formula (II)

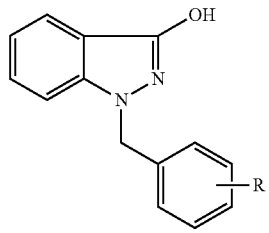

is subjected to reflux reaction with 1.2 mole of a compound of the formula $XCH(CO_2R')_2$ in the presence of 2.5 moles of potassium carbonate in glycol dimethyl ether solvent, to obtain a compound of the formula (III):

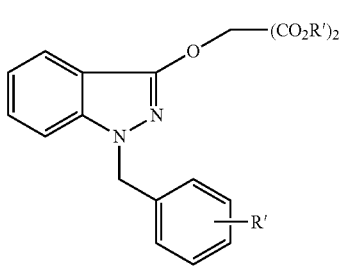
(III)

which is subjected to reflux hydrolysis in potassium hydroxide or sodium hydroxide solution, and then acidified to a pH of about 2 with diluted hydrochloric acid to produce a compound of the formula (I):

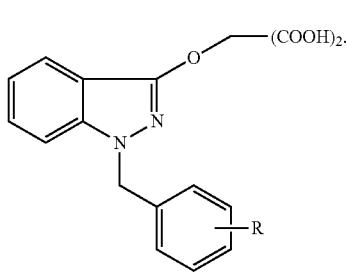
(I)

* * * * *